United States Patent [19]

Cokeley

[11] Patent Number: 5,030,092
[45] Date of Patent: Jul. 9, 1991

[54] METHOD AND APPARATUS FOR TEMPORARY ATTACHMENT OF A SAFETY LINE TO DENTAL RESTORATIONS AND APPLIANCES

[76] Inventor: Ricky R. Cokeley, 2626 Himes #5, Pueblo, Colo. 81005

[21] Appl. No.: 591,961

[22] Filed: Oct. 2, 1990

[51] Int. Cl.⁵ .............................................. A61C 3/00
[52] U.S. Cl. .................................... 433/141; 433/229
[58] Field of Search ................ 433/141, 163, 229, 26, 433/3, 102, 91

[56] References Cited

U.S. PATENT DOCUMENTS

| | | |
|---|---|---|
| 1,261,339 | 4/1918 | Angle . |
| 1,379,689 | 5/1921 | House . |
| 2,343,777 | 3/1944 | Lays . |
| 2,527,094 | 10/1950 | Goldfarb . |
| 4,129,456 | 12/1978 | Longo ................................. 433/229 |
| 4,504,229 | 3/1985 | Garito et al. ........................ 433/215 |
| 4,689,014 | 8/1987 | Krasner ............................... 433/215 |
| 4,773,857 | 9/1988 | Herrin ................................. 433/138 |
| 4,802,853 | 2/1989 | Krasner ............................... 433/215 |
| 4,822,278 | 4/1989 | Oliva et al. .......................... 433/91 |
| 4,834,654 | 5/1989 | Nussbaum .......................... 433/141 |
| 4,953,902 | 9/1990 | Brown ................................. 433/141 |

FOREIGN PATENT DOCUMENTS 2502928 7/1976 Fed. Rep. of Germany ...... 433/141
759648 2/1934 France ................................. 433/102

Primary Examiner—Cary E. Stone
Attorney, Agent, or Firm—John A. Beehner

[57] ABSTRACT

A dental appliance safety-line consists of a line, one end of which contains a flexible vinyl handle and with an attachment end. The vinyl handle is used to grasp onto and manipulate the safety line, and the attachment end provides an adequate amount of retentive surface area for an adhesive to penetrate and adhere to and imparts substantial strength between the safety line and a dental device such as a dental restoration or appliance. The safety line is left attached to the dental device during the fitting and adjustment procedures. Once the dental device is permanently affixed in the oral cavity, the chair side practitioner takes any readily available instrument and removes the safety line by cleaving the adhesive at the junction of the attachment end and surface of the dental device. This removal is accomplished without the need for modifying or refinishing the surface of the dental device.

21 Claims, 5 Drawing Sheets

METHOD AND APPARATUS FOR TEMPORARY ATTACHMENT OF A SAFETY LINE TO DENTAL RESTORATIONS AND APPLIANCES

BACKGROUND OF THE INVENTION

1. Technical Field

The present invention is directed to a method and apparatus for affixing a safety line to dental restorations and appliances. More particularly, the invention relates to a method and apparatus for temporarily bonding a safety line directly to a dental restoration or appliance so as to prevent the accidental ingestion or aspiration of restorations or appliances during the fitting or removal stage while still allowing the subsequent removal of the line when restorations or appliances are permanently affixed in the mouth, or removed from the mouth, without alteration or damage to the dental restorations or appliances.

2. Description of the Prior Art

Dental patients are placed in a reclined position in order to facilitate dental operating procedures. With patients in this position there is a high probability that objects placed in the patient's mouth by a dentist will fall toward the back of the mouth resulting in the aspiration or ingestion of the object.

This occurrence has potentially serious consequences, and has been well documented. Location and extraction of the dental object is costly and inconvenient in the best of circumstances, and has on occasion been fatal. As such, the fitting of dental restorations and appliances in the patient's mouth by a dentist poses substantial danger to the patient.

The dental profession has come to realize the danger posed to the patient by these objects and various methods have been advocated to prevent aspiration or ingestion, however, most have some drawbacks. Some experts advocate working with the patient in an upright position, but most modern practitioners find it extremely difficult to do so. The use of a rubber dam is suggested but it is impossible to perform many of the fitting procedures adequately with a rubber dam in place. Alternatively, gauze throat packs have been advocated but these are extremely uncomfortable and poorly tolerated by many patients. As such, these means though available are only partially effective, are often not employed because of time constraints, or significantly add to the discomfort of the patient.

The most effective means currently available to the profession to prevent the aspiration or ingestion of dental objects is to tie a piece of floss, string, or monofilament safety line to the appliance prior to introduction into the mouth. In this manner, even if the device does fall to the back of the throat, it can be easily retrieved by the dentist or assistant. Items such as dental bridges, endodontic files, and many intraoral instruments have retentive areas available which allow the securing of some type of safety line. Such retentive areas are often times a natural result of the design of the appliance itself as would be the case with a dental bridge. In other instances, a retentive area has been specifically designed into the instrument by the manufacturer.

Many dental objects, however, are smooth-surfaced and have no retentive area whatsoever. This precludes the routine attachment of any type of safety line.

The most common example of an appliance which does not lend itself to being secured with a safety line is an individual dental crown. This appliance poses convex surfaces with no available undercuts or tie-off points. Proper fitting of a crown requires the placement of the appliance on the tooth a number of times to examine its fit and function.

During each of these try-ins, the appliance can easily become dislodged from the tooth by the action of the patient's tongue or can slip from the operator's fingers. Since a safety line cannot be routinely secured, this occurrence has potentially serious consequences.

In addition to individual crowns, modern dentistry utilizes numerous other devices which are smooth-surfaced and provide no retentive undercuts for securing a safety line. Examples of such devices would include temporary crowns, pre-cast endo posts, cast endo posts and cores, and dental implant inserts.

Realizing the potential serious consequences posed by smooth-surfaced dental devices, some experts advocate the placement of retentive undercuts in the device during its fabrication. This retentive undercut is used to secure a safety line during the fitting stage but then must be removed by the dentist either before final cementation or once the appliance is permanently in place.

An example of this type of measure would be to incorporate a retentive button as part of the metal structure of a dental crown. This button is used to secure a safety line during the fitting and cementation stages. Once the device is in place, the dentist must take a cutting instrument and physically sever the retentive button from the crown. This area must then be smoothed and repolished to provide a clinically acceptable restoration.

This method of providing a means of securing dental devices with a safety line has several drawbacks. The fabrication of the button into the metal pattern requires a substantial amount of additional laboratory time. Also, even though the retentive button is available, often times this button is improperly utilized which leads to the risk of losing the device down the patient's throat even though steps have been taken to prevent this very accident.

Additionally, this button itself is a source of danger. During the try-in stage, the button projecting from the surface of the crown is sharp and can lacerate the patient's tongue or oral mucosa. Even more dangerous is the fact that if the object is aspirated or swallowed, this sharp projection protruding from an otherwise smooth dental device, could cause serious internal injury.

Finally, the button is often placed in a position which becomes inaccessible once the device is permanently placed and its removal requires substantial time by the dentist, and exposes the patient to the additional risk associated with the intraoral use of high speed cutting and polishing devices.

Another problem associated with incorporating a retentive button during fabrication is that many dental restorations are constructed of materials which do not permit the placement of such a button. Examples of these types of restorations would include veneers, crowns, and inlays constructed entirely of porcelain.

To date, research would indicate that there is no convenient, universally applicable, economical means of attaching a safety line to dental devices.

Ideally, a method should be available having the following features:

The method should allow the affixing of a safety line to any dental device regardless of the availability of retentive undercuts or tie-off points.

The method should be inexpensive.

The method should provide adequate bond strength between the dental device and the safety line.

The method should provide immediate bond strength between the dental device and the safety line.

The method should not require sophisticated instruments or equipment to achieve its bond.

The method should be reversible in that it produces no irreversible modifications to the dental device.

The method should be available to the manufacturer, the laboratory technician, or the dentist directly.

Ideally, a device should be available having the following features:

The device should be sufficiently strong to adequately retrieve a dislodged dental device.

The device should not interfere with the fitting and functional checks of the dental restoration or appliance.

The device should be inexpensive.

The device should allow for easy manipulation and placement on the dental restoration or appliance.

The device should assist in identifying a specific dental restoration or appliance.

The device should provide sufficient surface area at the bond interface to insure adequate strength between the dental device and the safety line.

The device should be easily removed from the dental restoration or appliance.

OBJECTS OF THE INVENTION

Accordingly, it is an object of the present invention to provide a method of securing a safety line to any dental device without the need for retentive undercuts or other securing points on the dental device.

Another object of the invention is to provide a safety line which can be secured to any dental device by a simple means without the use of sophisticated equipment or instruments.

Another object of the invention is to provide a safety line and a method of attaching a safety line which do not interfere with fitting and adjusting the dental device in an oral cavity.

Another object of the present invention is to provide a method that the safety line can be readily removed from the dental device once it is permanently placed in the oral cavity without altering the surface of the dental device and without reliance upon sophisticated cutting and polishing equipment.

Another object of the invention is to provide a method which instantly attaches a safety line to a dental device without the use of sophisticated instruments or equipment.

Another object of the present invention is to provide an inexpensive means of attaching a safety line to a dental device.

Another object of the present invention is to provide a sufficiently strong means of securing safety line to a dental device to allow retrieval of a dislodged dental device, thereby protecting the health of the patient.

Another object of the invention is to provide a device which can be readily manipulated and easily attached to a dental restoration or appliance by anyone.

Finally, it is another object of the present invention to provide means for identifying a specific dental restoration or appliance by providing safety lines of varying colors.

SUMMARY OF THE INVENTION

Briefly stated, the present invention consists of a safety line, one end of which contains a flexible vinyl handle and an attachment wick. The vinyl handle and attachment wick are an integral part of the safety line. The vinyl handle is used to grasp onto and manipulate the safety line. The attachment wick provides an adequate amount of retentive surface area for the adhesive to penetrate and adhere to. The wick, therefore, imparts substantial strength to the bond between the safety line and the dental device despite a relatively small surface area.

A small dab of cyanoacrylate gel is applied to the dental device at a location that will not interfere with anticipated fitting and adjustment procedures. Either fingers or forceps are used to grasp the vinyl handle of the safety line and the attachment wick is dipped into a cyanoacrylate accelerator.

The attachment wick is then pressed into the dab of cyanoacrylate gel on the dental device. A chemical reaction occurs and the safety line is immediately bonded onto the surface of the dental device. The safety line is left attached to the dental device during the fitting and adjustment procedures.

When the dental device is permanently affixed in the oral cavity, the chair side practitioner takes any readily available instrument and removes the safety line by cleaving the adhesive at the junction of the attachment wick and surface of the dental device. This removal is accomplished without the need for modifying or refinishing the surface of the dental device.

This same process can be accomplished by the use of a thermoplastic adhesive rather that a cyanoacrylate gel.

DESCRIPTION OF THE PREFERRED EMBODIMENT

A preferred embodiment of the present invention 10 is illustrated in FIGS. 1 through 10.

Figure 1:
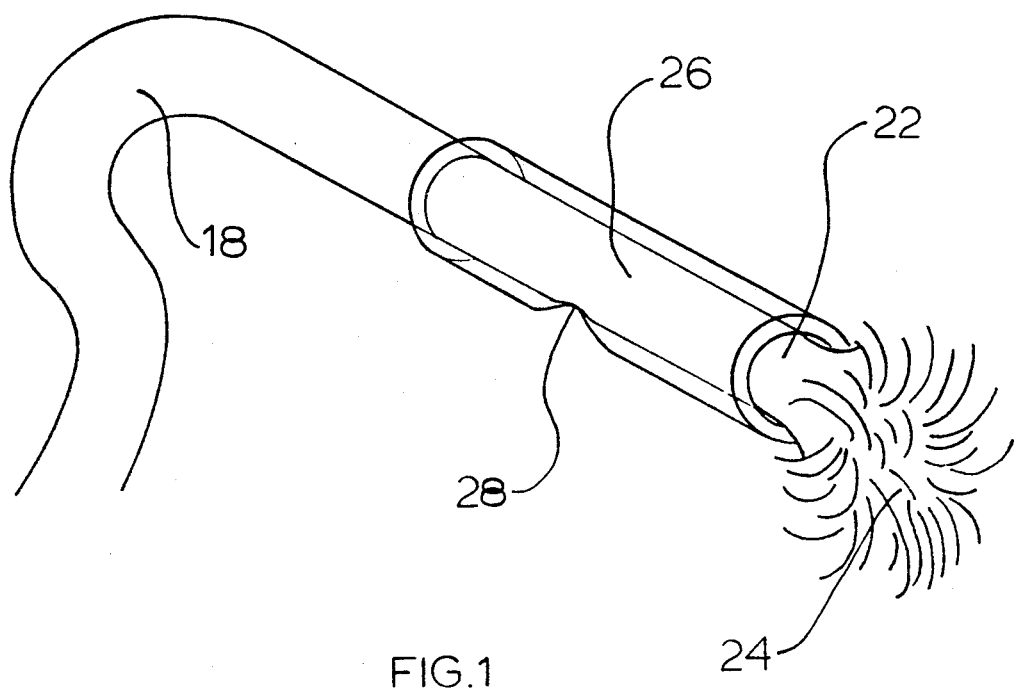
FIG. 1 is a foreshortened enlarged perspective view of one end of the safety-line.
Figure 2:
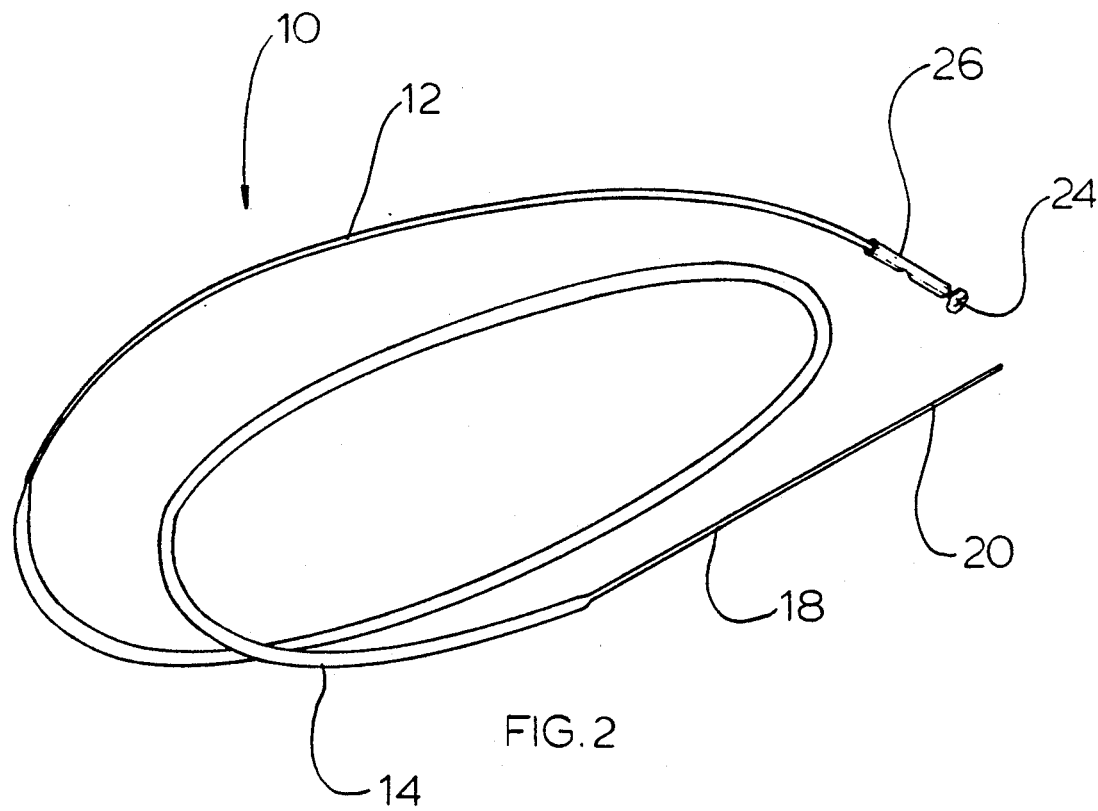
FIG. 2 is a perspective view of the safety-line of the invention.

The dental device safety line apparatus adapted to temporarily secure a dental restoration or appliance during a dental fitting procedure 10 is best illustrated by FIG. 2. FIG. 1 best illustrates the handle 26, wick end 22, and the wick 24 of the safety line 10.

The safety line 10 is preferably 66.5 cm long. The safety line 10 includes a 44.0 cm length of conventional unwaxed multifilament dental floss lead 12. Extending from the conventional dental floss lead 12, and integrally formed thereon, is a 16.0 cm length of flossing yarn 14. Extending from the flossing yarn 14, and integrally formed thereon, is a 3.5 cm length of conventional dental floss 18. Extending from the conventional floss threader lead 18, and integrally formed thereon, is a 3.0 cm floss threader 20 length (FIG. 2).

The conventional floss lead 12 has a wick end 22. Slipped over the wick end 22 of the conventional floss lead 12 of the safety line 10 is a 0.7 cm length of handle tubing 26. The handle tubing 26 is preferably formed of a clear length of semi-pliable vinyl tubing having an inside diameter equal to the outside diameter of the conventional floss lead 12.

The handle tubing 26 is placed approximately 0.1 cm from the wick end 22 of the conventional floss lead 12 and secured by a thermal weld crimp 28. It should also be apparent that the handle 26 might also be extruded over the floss during manufacture, or a length of semi-pliable material may be applied or integrated onto the external surface of the line adjacent the attachment end. The 0.1 cm length of exposed floss 12 is frayed to create an adhesive wick 24 (FIG. 1).

Figure 3:
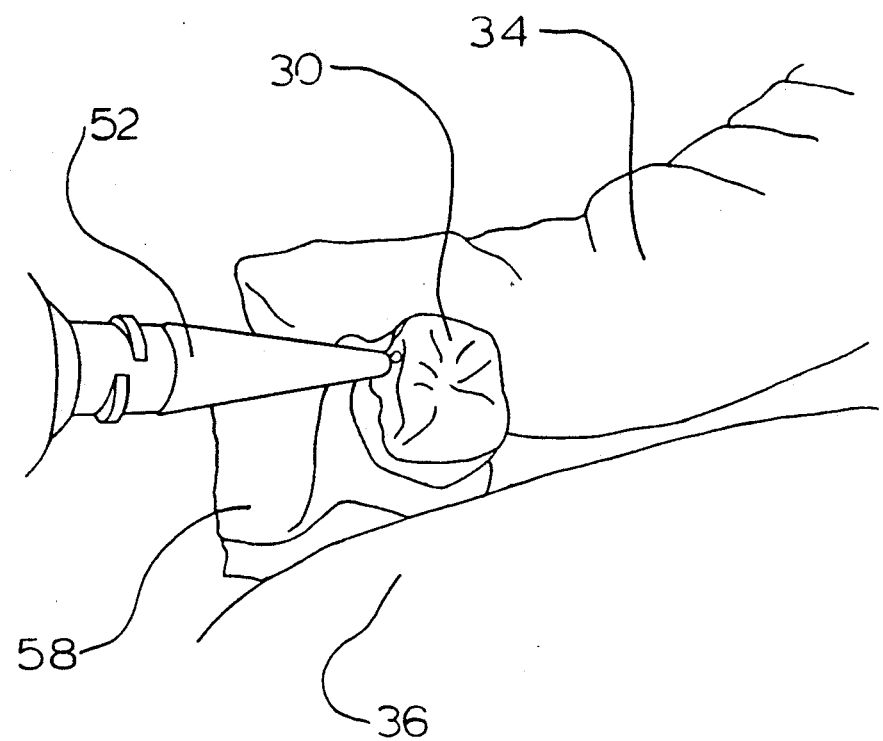
FIG. 3 is an enlarged perspective view showing adhesive being applied to a crown.

In operation, a small amount of cyanoacrylate bonding gel 60, may be applied from a container 52 to a crown 30 or other dental restoration or appliance (FIG. 3). The gel 60 may easily be applied to a crown 30 while retained on the crown die 58, and held between the thumb 34 and forefinger 36 of a laboratory technician or a chairside practitioner 32.

Figure 4:
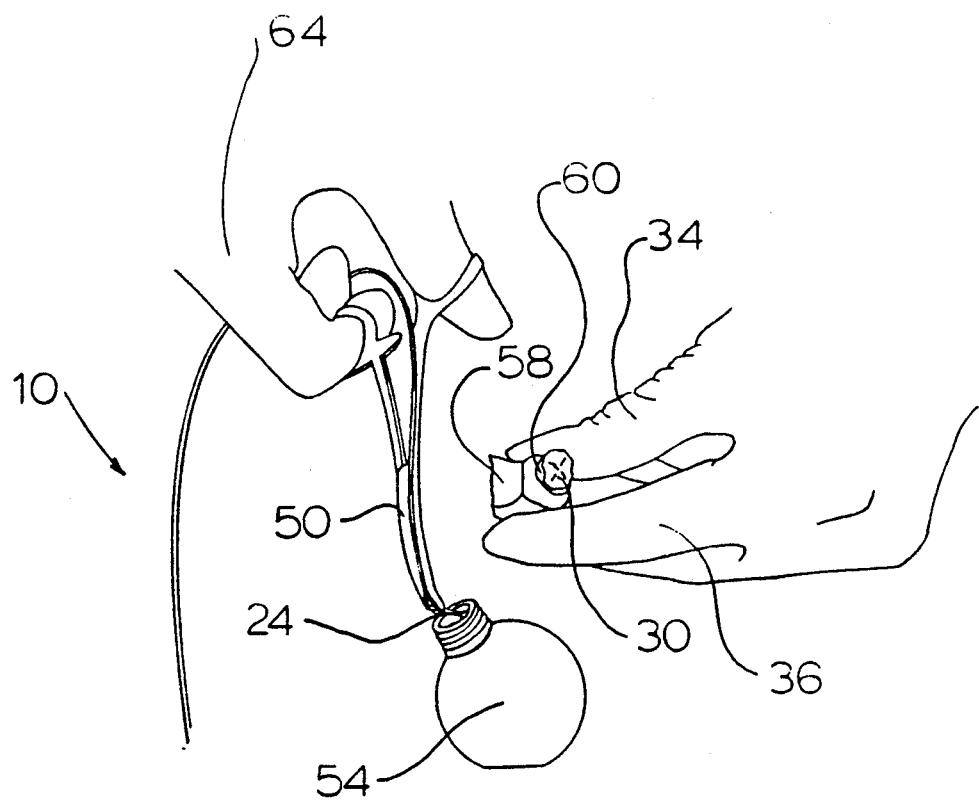
FIG. 4 is a partial perspective view showing the end of the safety line being dipped in an accelerator solution.

A technician or practitioner may then use a pair of forceps 50, in his or her free hand 64, to pick up the handle 26 of the safety line 10. The adhesive wick 24 of the safety line 10 may then be saturated with cyanoacrylate accelerator 62 from container 54 (FIG. 4).

Figure 5:
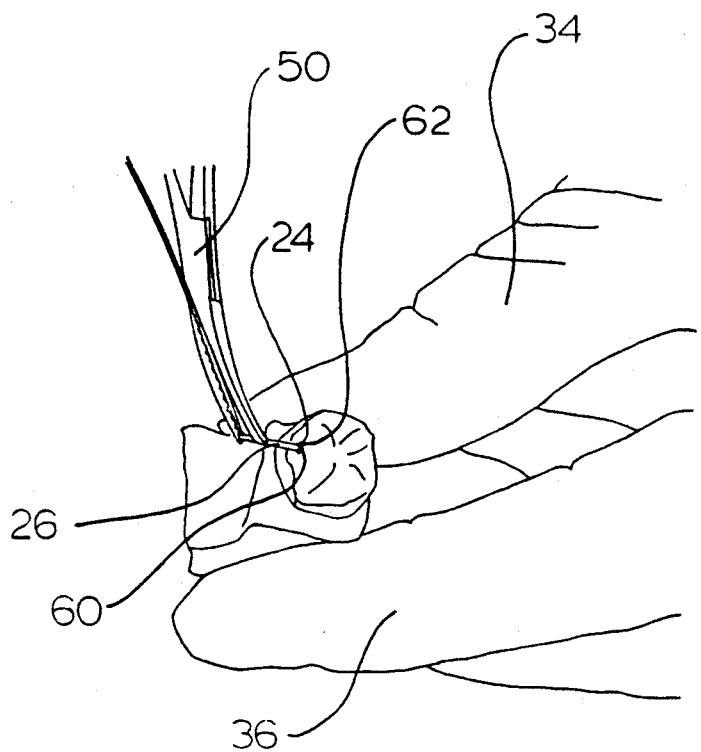
FIG. 5 is a partial perspective view showing the end of the safety line being placed in contact with the adhesive on a restoration.

The adhesive wick 24 saturated with accelerator 62 may then be pressed against the gel 60 on the crown 30 (FIG. 5). Once the adhesive has hardened the crown 30 may be removed from the crown die 58 and is ready for introduction into the oral cavity.

In the alternative, it is apparent that the accelerator may be placed on the dental appliance and the cyanoacrylate onto the attachment end, thereby reversing the attachment process but achieving substantially the same result.

Once chairside, the safety line 10 may then be clipped with the bib clip 48 of the bib harness 46 of a patient 38 wearing a dental bib 44. In this fashion the crown 30 is safely anchored. Should the crown 30 be accidentally dislodged in the oral cavity during fitting it may be recovered without harm to the patient 38.

Figure 6:
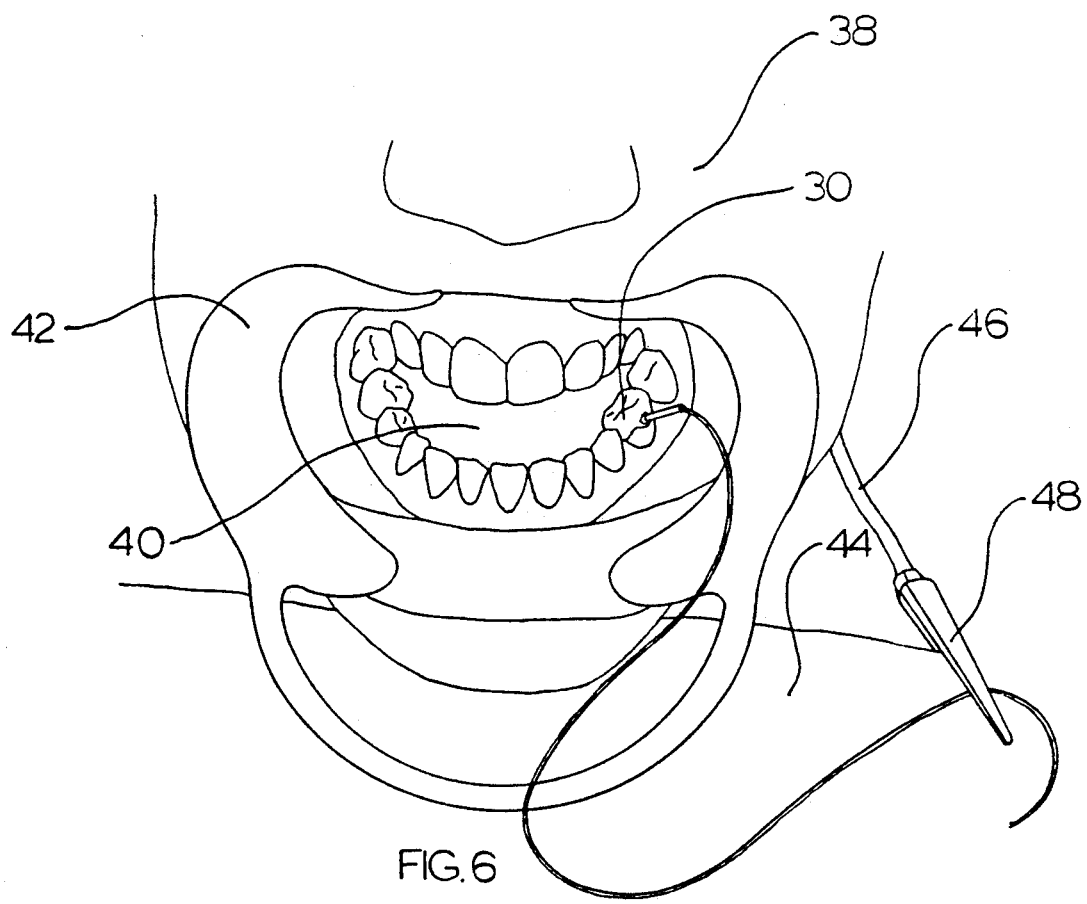
FIG. 6 illustrates the appliance in place in a patient's mouth with the safety line extending therefrom and secured by the clip for the patient's bib.

The patient 38, with their mouth 40 isolated by a mouth prop 42, may then be safely trial fitted with the crown 30 (FIG. 6). Once appropriate fit and function of the crown 30 has been tested, the crown may be permanently cemented in the patient's oral cavity 40.

Figure 7:
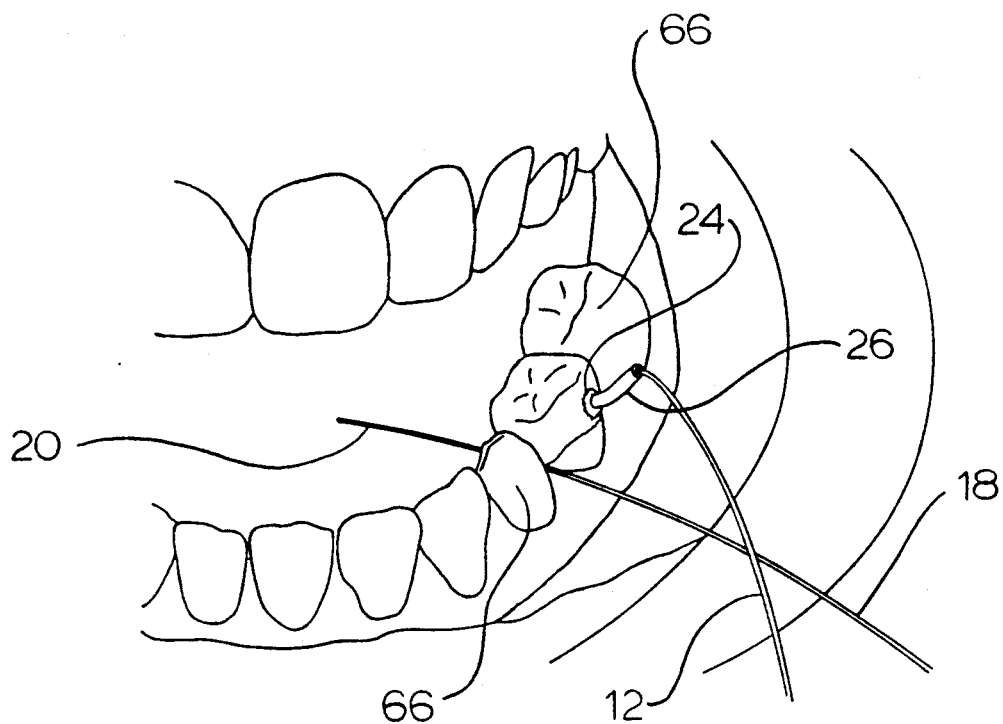
FIG. 7 shows the free-end or threader portion of the safety line being inserted between the appliance and adjacent tooth for removal of excess cement.
Figure 8:
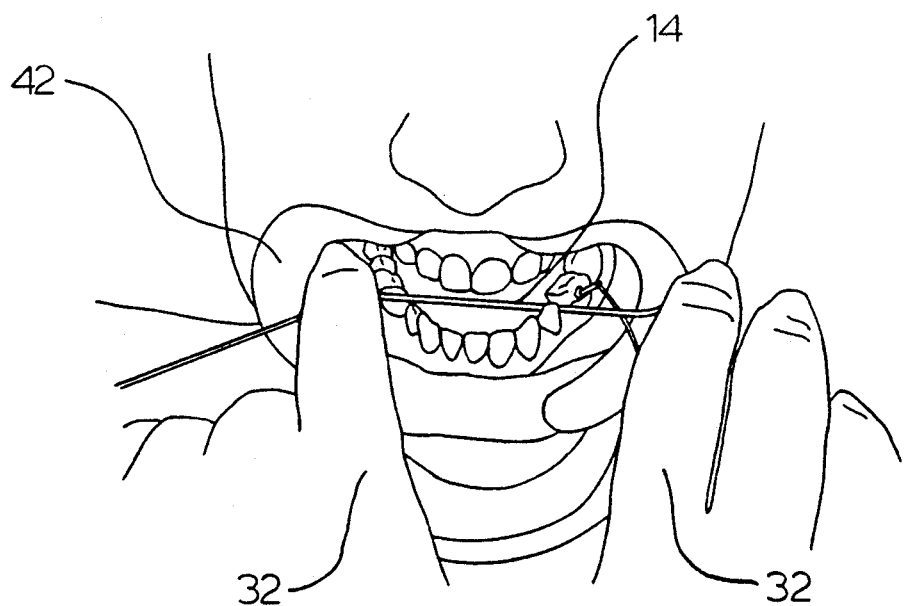
FIG. 8 illustrates use of the floss yarn (super floss) portion of the safety line for debridement.

After the crown cement has hardened the floss lead 12 may be passed between the crown 30 and adjacent tooth 66. The flossing yarn 14 of the safety line 10 may then be used to remove excess cement from the interproximal sulcus and contact area (FIGS. 7 and 8). Additionally, the floss threader 20 may be passed underneath an occluded contact point so as to dislodge residual cement occlusally (FIGS. 7 and 8).

Figure 9:
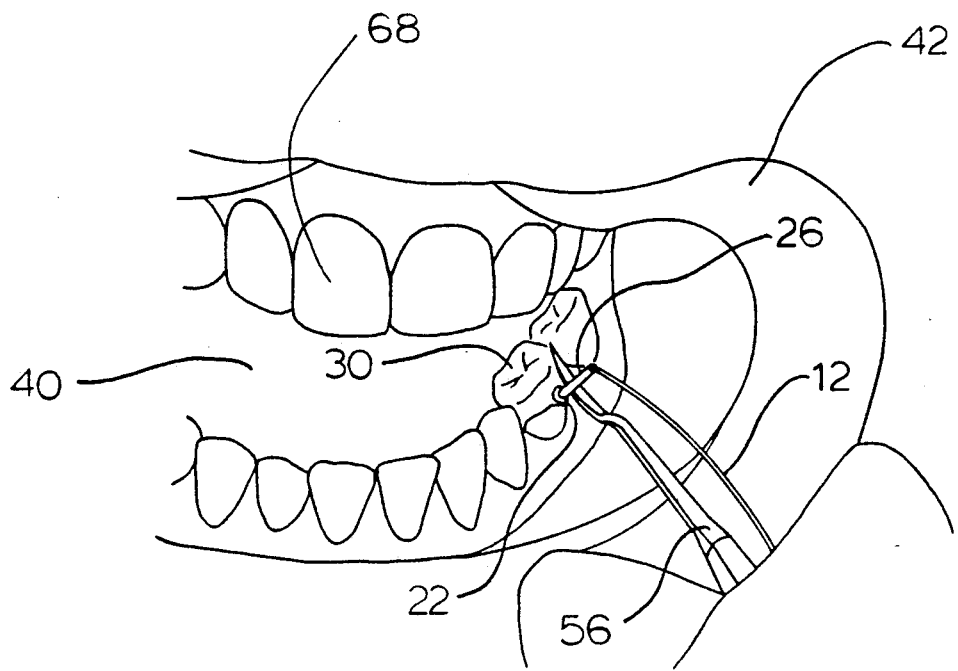
FIG. 9 is a perspective view showing the safety line being cleaved from the installed appliance.
Figure 10:
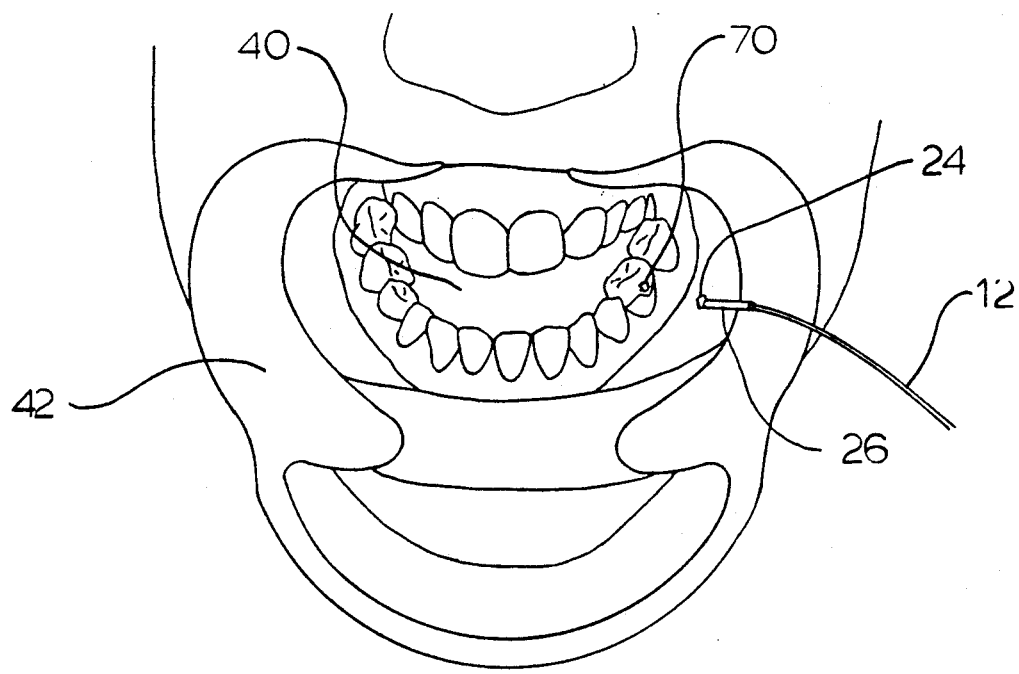
FIG. 10 is a partial perspective view showing the severed safety line being withdrawn from the patient's mouth.

The safety line 10 is preferably removed with a sharp curette 56 or scaler (FIG. 9). Once the safety line 10 is removed a small amount of adhesive 70 may remain on the crown 30 (FIG. 10). This adhesive 70 may easily be removed with a curette 56 or scaler.

Figure 11:
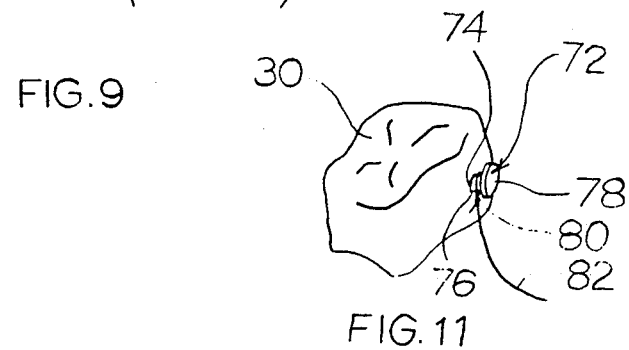
FIG. 11 is a perspective view of a dental attachment button adapted for securement to a dental appliance or restoration.

In the alternative, a button 72 may be provided (FIG. 11). In a preferred embodiment the button 72 has an attachment end 74 adapted to be adhered to a dental appliance or restoration. The button 72 also has a shaft 76, and a retention cap 78.

The attachment end 74 of the button 72 may be adhered to a dental appliance or restoration 30 in the manner herein described before. After the button 72 has been adhered to the dental restoration or appliance 30 a loop 80 of conventional dental floss 82, or the like, may be passed over the retention cap 78 and cinched about the shaft 76.

Once the dental device 30 has been affixed or removed from a patient's mouth the button 72 may be removed from the dental device 30 as has been described hereinbefore.

It should be noted that the button 72 differs from prior art buttons in that the prior art teaches only buttons that are integrally formed into dental appliances or restorations 30. These buttons must be machined away in order to produce a clinically acceptable surface and are not adapted to be adhered to appliance or restoration surfaces.

While the invention has been described with a certain degree of particularity, it is manifest that many changes may be made in the details of construction and the arrangement of components without departing from the spirit and scope of the disclosure. It is understood that the invention is not limited to the embodiments set forth herein for purposes of exemplification, but is to be limited only by the scope of the appended claims including the full range of equivalency to which each element thereof is entitled.

For example, a method is also foreseen wherein a handle having a retentive loop might be directly adhered to a dental restoration or appliance thereby allowing a piece of conventional dental floss to be attached to the retentive loop.

Additionally, the attachment end of the device might terminate in a small suction cup, sponge, knot, or the like. Likewise, different colors of floss may be provided so as to aid identification of multiple restorations.

It is also apparent that the handle portion is not critical to the invention, but is provided primarily to facilitate manipulation of the apparatus 10.

Thus, there has been shown and described an improved method and apparatus for temporary attachment of a safety line to dental restorations and appliances which accomplishes at least all of the stated objects.

I claim:

1. A method of temporarily securing a dental apparatus, adapted for insertion into the mouth, against accidental ingestion or aspiration during a dental procedure, said method comprising:

providing a safety line including an elongated flexible line and a safety line attachment means, having said elongated flexible line attached to said safety line attachment means, applying an adhesive to at least one of said attachment means and said dental apparatus, engaging said attachment means with the dental apparatus with adhesive disposed between them; thereby bonding said attachment means to said dental apparatus;

performing a dental procedure with said dental apparatus, and removing said attachment means from said dental apparatus.

2. The method of claim 1, wherein said adhesive applying step comprises the steps of:

applying a small amount of cyanoacrylate gel to the surface of the dental apparatus; and applying a small amount of cyanoacrylate accelerator to the safety line attachment means.

3. The method of claim 1, wherein said adhesive applying step comprises the steps of:

applying a small amount of cyanoacrylate accelerator to the surface of the dental apparatus; and applying a small amount of cyanoacrylate gel to the safety line attachment means.

4. The method of claim 1, wherein said removing step comprises the steps of:

cleaving the adhesive at its attachment site on said dental apparatus; and scaling the attachment site to remove any residual adhesive on said dental apparatus.

5. The method of claim 4, wherein said removing step further comprises the step of polishing the attachment site to remove any residual adhesive on said dental apparatus.

6. The method of claim 1 wherein said dental procedure comprises inserting and fitting said dental apparatus into a patient's mouth.

7. The method of claim 1 wherein said dental procedure comprises removing said dental apparatus from a patient's mouth.

8. The method of claim 1 wherein said attachment means comprises one end of said safety line.

9. The method of claim 1 wherein said attachment means comprises a handle including a loop for attachment to said elongated flexible line.

10. The method of claim 1 wherein said attachment means comprises a button of a shape to accommodate tying said elongated flexible line thereto.

11. The method of claim 1, wherein the adhesive applied in said adhesive applying step is a thermoplastic material.

12. The method of claim 1 further comprising anchoring said safety line.

13. A dental device safety line apparatus adapted to temporarily secure a dental apparatus during a dental procedure, comprising:

a flexible safety line having a securement end adapted for anchoring said line and an opposing attachment end adapted to be adhered to a dental apparatus, and a handle on said line adjacent said attachment end whereby said handle may be grasped by a dental instrument for manipulating said safety line.

14. The dental device safety line apparatus of claim 13, wherein said handle further comprises a length of tubing surrounding said safety line and secured thereto adjacent said attachment end.

15. The dental device safety line apparatus of claim 14, wherein said length of tubing is formed of a plastic material.

16. The dental device safety line apparatus of claim 14, wherein said tubing is pinch anchored to said safety line.

17. The dental device safety line apparatus of claim 13, wherein said attachment end is formed by fraying one end of said safety line.

18. The dental device safety line apparatus of claim 13, wherein at least some portion of said safety line is formed of a length of flossing yarn.

19. The dental device safety line apparatus of claim 13, further comprising a floss threader attached to said securement end of said safety line.

20. The dental device safety line apparatus of the claim 13, wherein said safety line is formed of dental floss.

21. The dental device safety line apparatus of claim 13, wherein said safety line is formed of monofilament.

* * * * *